United States Patent [19]
Vere Hodge

[11] Patent Number: 6,051,579
[45] Date of Patent: Apr. 18, 2000

[54] USE OF 2-AMINO PURINE DERIVATIVES FOR THE TREATMENT AND PROPHYLAXIS OF HUMAN HERPES VIRUS 7 INFECTION

[75] Inventor: Richard Anthony Vere Hodge, Reigate, United Kingdom

[73] Assignee: SmithKline Beecham plc, Brentford, United Kingdom

[21] Appl. No.: 09/209,666

[22] Filed: Dec. 10, 1998

Related U.S. Application Data

[63] Continuation of application No. 08/513,767, filed as application No. PCT/GB94/02486, Nov. 11, 1994.

[30] Foreign Application Priority Data

Nov. 12, 1993 [GB] United Kingdom .................. 9323404

[51] Int. Cl.$^7$ ............................ A01N 43/90; A01N 57/00
[52] U.S. Cl. ............................................. 514/262; 514/81
[58] Field of Search ....................................... 514/262, 81

[56] References Cited

FOREIGN PATENT DOCUMENTS

| 0 141 927 | 5/1985 | European Pat. Off. . |
|---|---|---|
| 0 182 024 | 5/1986 | European Pat. Off. . |
| 0 216 459 | 4/1987 | European Pat. Off. . |
| 0 458 363 | 11/1991 | European Pat. Off. . |
| WO A 9200742 | 1/1992 | WIPO . |

OTHER PUBLICATIONS

Fields BN et al., Fields Virology, Chapter 15, 3rd Ed, vol. 1, pp.436. (1996).
Boyd et al., Antiviral Chem. Chemotherapy, Suppl. 4(1), pp. 3–11 (1993).
Luppi et al., Haematologica, 81(3), pp. 265–281 (1996).
Akesson–Johnsson et al., Antimicrobial Agents and Chemotherapy, Dec. 1990, vol. 34(12) pp. 2417–2419.
Lui et al., Antiviral Chemistry and Chemotherapy (1990), 1(5), pp. 313–318.
Agut et al., Institut, Pasteur/Elsevier (1989) 140 (3), pp. 219–228.
Abashi D.V. et al. In Vivo, vol. 5 (3), 1991, pp. 193–200.
J.B. Black et al., Virus Research 52 (1997) pp. 25–41.
Vere Hodge RA. et al., Antiviral Chemistry and Chemotherapy (1993) 4 Suppl. 1, pp. 13–24.
Earnshaw D.L. et al., Antimicrobial Agents and Chemotherapy (1992) 36, pp. 2747–2757.
Vere Hodge et al., Antimicrobial Agents and Chemotherapy (1989) 33, pp. 223–229.
Boyd et al., Antimicrobial Agents and Chemotherapy (1987) 31, pp. 1238–1242.
Larsson A. et al, Antimicrobial Agents and Chemotherapy (1986) 30. pp. 598–605.
Fields B.N. et al., Fields Virology, Chapter 71, pp. 2221 (1996).
Harnden et al. J. Chem. Soc. Perkin Trans. I, (1988), 10, pp: 2777–2784.
J. Nickolas, "Determination and Analysis of the Complete Nucleotide Sequence of Human Herpevirus 7", J. of Virology, 70(9), pp. 5975–5989 (1996).
Berneman, et al., "Human Herpesvirus 7 is a T–Lymphotropic Virus and is related to, but significantly Different from Human Herpevirus 6 and Human Hytomegalovirus," Proc. Natl. Acad. Sci., USA, 89, pp. 10552–10556 (1992).
Harnden et al., vol. 110 CA (1989) 173658p.
Frendel, et al., "Human Herpesvirus 7", Fields Virology, 3rd Edition, pp. 2609–2622.
Tippie et al 102 CA:214686, 1984.

*Primary Examiner*—Russell Travers
*Attorney, Agent, or Firm*—Dara L. Dinner; Stephen Venetianer; Charles M. Kinzig

[57] ABSTRACT

The use of a compound of formula (A):

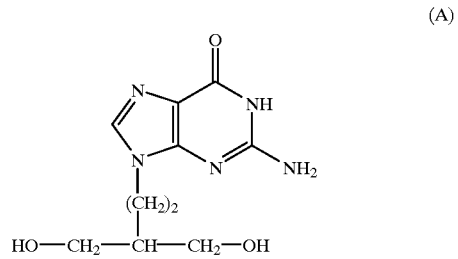

or a bioprecursor, or a pharmaceutically acceptable salt, phosphate ester and/or acyl derivative of either of the foregoing in the manufacture of a medicament for use in the treatment (including prophylaxis) of HHV-7 infection.

4 Claims, No Drawings

USE OF 2-AMINO PURINE DERIVATIVES FOR THE TREATMENT AND PROPHYLAXIS OF HUMAN HERPES VIRUS 7 INFECTION

This application is a continuation of application Ser. No. 08/513,767 filed Oct. 31, 1995, which is a 371 of PCT/GB94/02486, filed Nov. 11, 1994 which claims priority from GB9323404.5 filed Nov. 12, 1993.

This invention relates to treatment of infection caused by human herpesvirus 7 (HHV-7), and to the use of compounds in the preparation of a medicament for use in the treatment of such conditions.

When used herein, 'treatment' includes prophylaxis as appropriate.

EP-A-141927 (Beecham Group p.l.c.) discloses penciclovir, the compound of formula (A):

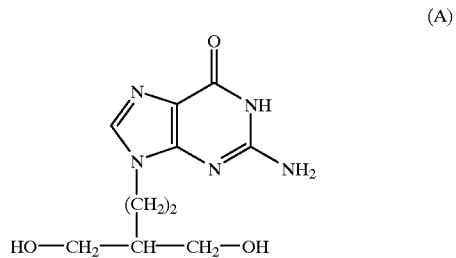

(A)

and salts, phosphate esters and acyl derivatives thereof, as antiviral agents. The sodium salt hydrate of penciclovir is disclosed in EP-A-216459 (Beecham Group p.l.c.). Penciclovir and its antiviral activity is also disclosed in Abstract P.V11-5 p.193 of 'Abstracts of 14th Int. Congress of Microbiology', Manchester, England 7-13 September 1986 (Boyd et. al.).

Orally active bioprecursors of the compound of formula (A) are of formula (B):

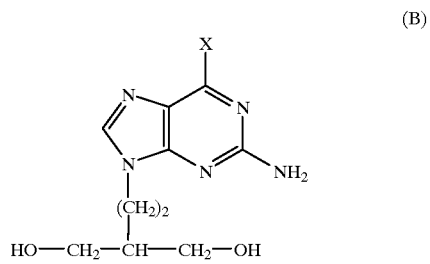

(B)

and salts and derivatives thereof as defined under formula (A); wherein X is $C_{1-6}$ alkoxy, $NH_2$ or hydrogen. The compounds of formula (B) wherein X is $C_{1-6}$ alkoxy or $NH_2$ are disclosed in EP-A-141927 and the compounds of formula (B) wherein X is hydrogen, disclosed in EP-A-182024 (Beecham Group p.l.c.) are preferred prodrugs. A particularly preferred example of a compound of formula (B) is that wherein X is hydrogen and wherein the two OH groups are in the form of the acetyl derivative, described in Example 2 of EP-A-182024, hereinafter referred to as famciclovir.

The compounds of formulae (A) and (B) and salts and derivatives thereof have been described as potentially effective in the treatment of infections caused by herpesviruses, such as herpes simplex type 1, herpes simplex type 2, varicella-zoster, Epstein-Barr viruses, and cytomegalovirus.

Human herpesvirus 7 (HHV-7) is a recently discovered member of the family Herpesviridae. The virus was first isolated in 1989 from the peripheral blood lymphocytes (PBL) of a healthy individual that were being cultured under conditions that lead to T-cell activation.

Analysis of restriction endonuclease profiles of the viral DNA indicated that the new agent differed from the other known human herpesviruses. Since then, HHV-7 has been isolated from the saliva of as many as 75% of healthy adults. Antibodies to HHV-7 can be detected in serum specimens from approximately 90% of the normal population and seroconversion usually occurs during childhood after the age of 2.

It is possible that HHV-7 may play a role in the activation of human immunodeficiency virus (HIV-1).

It has now been discovered that the above compounds have potential activity against HHV-7.

Accordingly, the present invention provides a method of treatment of HHV-7 infection in humans, which method comprises the administration to the human in need of such treatment, an effective amount of a compound of formula (A):

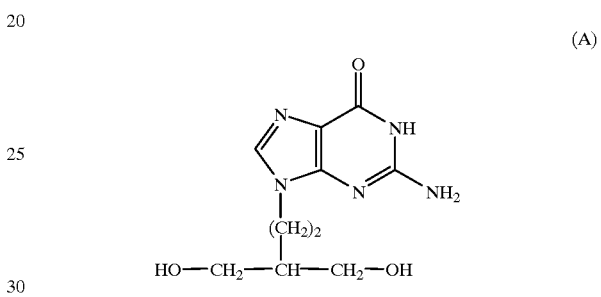

(A)

or a bioprecursor, or a pharmaceutically acceptable salt, phosphate ester and/or acyl derivative of either of the foregoing.

The term 'acyl derivative' is used herein to include any derivative of the compounds of formula (A) in which one or more acyl groups are present. Such derivatives are included as bioprecursors of the compounds of formula (A) in addition to those derivatives which are per se biologically active.

The compound of formula (A) may be in one of the forms disclosed in EP-A-216459 (Beecham Group p.l.c.).

Examples of bioprecursors, pharmaceutically acceptable salts and derivatives are as described in the aforementioned European Patent references, the subject matter of which are incorporated herein by reference.

A particular compound of formula (B) of interest is 9-(4-acetoxy-3-acetoxymethylbut-1-yl)-2-aminopurine, known as famciclovir (FCV), the well-absorbed oral form of penciclovir (PCV).

The compound of formula (A), bioprecursors, salts and derivatives may be prepared as described in the aforementioned European Patent references.

The compound, in particular, famciclovir, may be administered by the oral route to humans and may be compounded in the form of syrup, tablets or capsule. When in the form of a tablet, any pharmaceutical carrier suitable for formulating such solid compositions may be used, for example magnesium stearate, starch, lactose, glucose, rice, flour and chalk. The compound may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavouring or colouring agents may be added to form syrups.

For parenteral administration, fluid unit dose forms are prepared containing the compound and a sterile vehicle. The compound depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

Preferred parenteral formulations include aqueous formulations using sterile water or normal saline, at a pH of around 7.4 or greater, in particular, containing penciclovir sodium salt hydrate.

As is common practice, the compositions will usually be accompanied by written or printed directions for use in the medical treatment concerned.

An amount effective to treat the virus infection depends on the nature and severity of the infection and the weight of the mammal.

A suitable dosage unit might contain from 50 mg to 1 g of active ingredient, for example 100 to 500 mg. Such doses may be administered 1 to 4 times a day or more usually 2 or 3 times a day. The effective dose of compound will, in general, be in the range of from 0.2 to 40 mg per kilogram of body weight per day or, more usually, 10 to 20 mg/kg per day. In the case of famciclovir, the dosage unit would be 250 mg, 500 mg or 750 mg, preferably 250 mg or 500 mg.

The present invention also provides the use of a compound of formula (A) or a bioprecursor, or a pharmaceutically acceptable salt, phosphate ester and/or acyl derivative of either of the foregoing, in the preparation of a medicament for use in the treatment of HHV-7 infection. Such treatment may be carried out in the manner as hereinbefore described.

The present invention further provides a pharmaceutical composition for use in the treatment of HHV-7 infection, which comprises an effective amount of a compound of formula (A) or a bioprecursor, or a pharmaceutically acceptable salt, phosphate ester and/or acyl derivative of either of the foregoing, and a pharmaceutically acceptable carrier. Such compositions may be prepared in the manner as hereinafter described.

The compound of formula (A) and its prodrugs show a synergistic antiviral effect in conjunction with interferons; and treatment using combination products comprising these two components for sequential or concomitant administration, by the same or different routes, are therefore within the ambit of the present invention. Such products are described in EP-A-271270 (Beecham Group p.l.c.).

An assay method involving the inhibition of a cytopathic effect in human cord blood cells is conducted at a dose range of 0.01 $\mu$M–100 $\mu$M. The general procedure is as described for HHV-7, in Chapter 23 of Human Herpesvirus; Epidemiology, Molecular Biology and Clinical Pathology— Conference Proceedings, Ablashi D. V. (Ed).

Evaluation of PCV against HHV-7 in Human Cord Blood Cells[a]

Human mononuclear cells were isolated from umbilical cord blood and inoculated in triplicate with the test virus. One hour later, duplicate dilutions of the compound were added, resulting in 5, 10, 50, or 100 $\mu$M final concentrations. After 3–6 days, cellls were removed and tested for the presence of virus by indirect immunofluorescence (IFA) using type specific monoclonal antibodies. Three fields of 100 cells each were read from each sample.

|  |  | HRV-7 Strain SB | | |
| --- | --- | --- | --- | --- |
| Compound | Conc $\mu$M | % Inf Day 4 | % Inf Day 7 | % Inhib Day 7 |
| Uninfected |  | 0 | 0 |  |
| Infected |  | 4 | 49 |  |
| PCV | 5 | 4 | 42 | 21 |
|  | 10 | 3 | 35 | 30 |
|  | 50 |  | 34 | 29 |
|  | 100 |  | 36 | 31 |

[a]Dilutions of the compounds were added 1 hr after viral inoculation of human cord blood. The % infected cells was measured by anti-complement immunofluorescence (ACIF). All numbers are averages of results of cord blood from 3 donors and triplicate readings were performed on each sample. Each reading represents actual counting of 3 fields.

I claim:

1. A method for the treatment (including prophylaxis) of HHV-7 infection in mammals, including humans, which method comprises administering to the mammal in need of such treatment, an effective amount of a compound of formula (A):

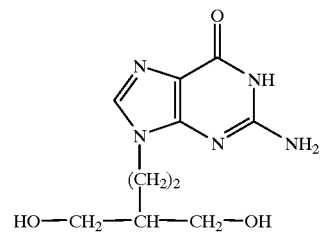

or a bioprecursor, or a pharmaceutically acceptable salt, phosphate ester and/or acyl derivative of either of the foregoing.

2. A method according to claim 1 wherein the treatment is for HHV-7 infection in patients infected with human immunodeficiency virus.

3. A method according to claim 1 wherein the compound is famciclovir.

4. A method according to claim 3 wherein famciclovir is administered at a dose of 250 mg, 500 mg or 750 mg, two or three times a day.

* * * * *